United States Patent
Sundström et al.

(12)

(10) Patent No.: US 6,891,025 B2
(45) Date of Patent: May 10, 2005

(54) MODIFIED CYTOKINE RECEPTOR PROTEIN

(75) Inventors: Michael Sundström, Stockholm (SE); Gunnar Norstedt, Bromma (SE)

(73) Assignee: Pharmacia AB, Stockholm (SE)

( * ) Notice: Subject to any disclaimer, the term of this patent is extended or adjusted under 35 U.S.C. 154(b) by 154 days.

(21) Appl. No.: 09/355,664

(22) PCT Filed: Feb. 17, 1998

(86) PCT No.: PCT/SE98/00277

§ 371 (c)(1),
(2), (4) Date: Oct. 8, 1999

(87) PCT Pub. No.: WO98/35991

PCT Pub. Date: Aug. 20, 1998

(65) Prior Publication Data

US 2003/0009009 A1 Jan. 9, 2003

(30) Foreign Application Priority Data

Feb. 18, 1997 (SE) .............................................. 9700566

(51) Int. Cl.$^7$ ........................ A61K 38/24; A61K 38/27; C07K 1/00
(52) U.S. Cl. ...................... 530/399; 530/350; 530/418; 514/2
(58) Field of Search ................................ 530/350, 351, 530/397, 399, 418

(56) References Cited

PUBLICATIONS

Muller, Y.A. et al. J. Mol.Biol. (1996) 256, 144–159.*
Kaczmarski et al Abstract, "The Cytokine Receptor Superfamily," Blood Rev., 5 (3):193–203 (1991).
Sundström et al, Journal of Biological Chemistry, 271(50):32197–32203 (Dec. 13, 1996).
DeVos et al, Science, 255:306–312 (1992).
WPI Abstract of JP 6172394 dated Jun. 21, 1994.

* cited by examiner

Primary Examiner—John Ulm
Assistant Examiner—Olga N. Chernyshev
(74) Attorney, Agent, or Firm—Dinsmore & Shohl LLP (57) ABSTRACT

A modified extracellular domain of a cytokine receptor is capable of being crystallized without being complexed to a ligand molecule. The receptor preferably is a homo- or heterodemeric receptor having at least one molecule segment which contributes to a disorder structure deleted. A preferred receptor is human growth hormone receptor (hGHR).

2 Claims, 2 Drawing Sheets

MODIFIED CYTOKINE RECEPTOR PROTEIN

RELATED APPLICATION

This application is the National Stage Entry of PCT/SE98/00277 filed Feb. 17, 1988.

FIELD OF INVENTION

The present invention relates to modified extracellular domains of cytokine receptor proteins which are capable of being crystallized without being complexed to a ligand molecule, methods of preparing such proteins and crystals formed of the modified proteins.

BACKGROUND OF THE INVENTION

Figure 1:
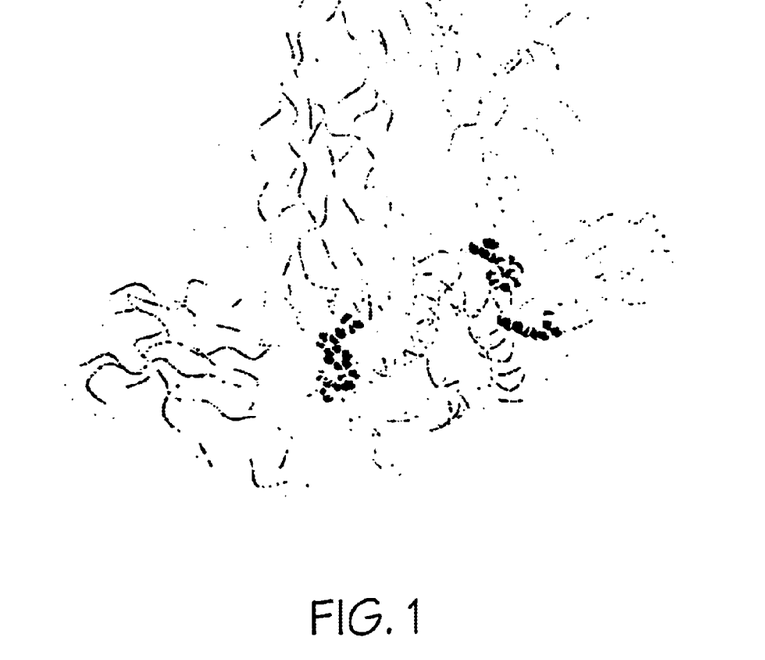
FIG. 1 schematically illustrates the general features of the hGH:hGHR 1:2 complex.

Human growth hormone (hGH) is a key factor in the regulation of certain physiological processes, such as growth and differentiation of muscle and bone cells. The hGH signal is mediated by homodimerization of two identical human growth hormone receptors (hGHR), Wells, et al, *Annu. Rev. Biophys. Biomol. Struct.*, 22, 329–51 (1993). To accomplish this task, hGH interacts with each receptor using two distinct binding epitopes (hGH site 1 and 2), that both bind at the domain interface of the extracellular part of the receptor, deVos et al, *Sciences*, 255, 306–12 (1992) (FIG. 1). However, an important and hitherto unresolved question is if the receptor undergoes conformational changes to facilitate hGH binding. hGH binds to the hGHR but also to its naturally occurring soluble binding protein (hGHbp), Bauman et al, *J. Clin. Endocrinol. Metab.*, 78, 1113–8 (1994). Heterologously expressed variants of hGHbp are therefore commonly used to study the extracellular events in receptor dimerization, Fuh et al, *J. Biol. Chem.*, 265, 3111–5 (1990). Moreover, in a zinc dependent interaction, hGH also can bind to the human prolactin receptor (hPRLR), Cunningham et al, *Science*, 250, 1709–12 (1990).

It would be highly desirable to obtain a model to study the structural requirements for the transition of the extracellular part of the human growth hormone receptor from its free, unliganded state to its homodimeric state complexed with a ligand. Such studies could potentially lead to a more detailed understanding of the binding conditions specific for hGHR and would constitute important means in obtaining new drug candidates with ligand activity. However, it has so far been impossible to perform binding studies of hGHR in crystalline form without having the receptor molecule bound to a natural ligand. The reason is that both hGHR and other cytokine receptors have been found difficult to crystallize in their unliganded form, since they most likely contain domains and/or loop regions that are flexibly connected which contributes to a disordered state which obstructs crystallization.

It is the object of the present invention to provide modified extracellular domains of cytokine receptors which solve the described problems and which are capable of being crystallized with conventional methods. Furthermore, it is an object of the present invention to provide crystals of modified extracellular receptor proteins which are exceptionally useful for binding studies with small molecules that, in the absence of the natural ligand, are free to interact with the receptor binding surfaces.

SUMMARY OF THE INVENTION

According to a first aspect, the present invention is directed to a modified extracellular domain of a cytokine receptor protein, capable of being crystallized without being complexed to a ligand molecule. These modified proteins substantially maintain their activity to their native ligands and they will therefore constitute powerful tools for ligand interaction studies. The inventive, modified cytokine receptor preferably is of the type which oligomerizes when being bound to a ligand. This may include heterooligomerization of homodimerization, as discussed in *Mol. Cell. Biol.*, 1994, Vol. 14(6), p.3535–49: S Watowich et al. Most preferably, the modified receptor is a homodimeric cytokine receptor, such as the growth hormone receptor (hGHR) having an extracellular part consisting of 237 amino acids in its native state. The inventive proteins have at least one molecule segment contributing to a disordered structure deleted. Preferably, the deletion results in a truncation in at least one terminal end and most preferably it is truncated both in its C-terminal end and in its N-terminal end. More preferably, the inventive proteins are modified human growth hormone receptors (hGHR) with 31 or 33 amino acid residues removed in its N-terminal end and/or with 3 or 4 amino acid residues removed in its C-terminal end. Even more preferably, the inventive modified human growth hormone receptor (hGHR) consists of the amino acid residues 32–237 (SEQ ID NO: 2), 32–234 (SEQ ID NO: 3), or 34–233 (SEQ ID NO: 4) of the native molecule. Of these modified molecules, the truncated receptor consisting of amino acids 32–234 (SEQ ID NO: 3) of the native molecule is the most preferred. It should be emphasized that said modified cytokine receptors would be readily produced by the skilled person with existing methods of recombinant technology and their production in a recombinant host and their subsequent purification, therefore are not parts of the present invention. Further aspects of the invention are disclosed below.

DETAILED DESCRIPTION

In addition to the above-noted aspects, according to another aspect, the present invention relates to crystals of unliganded modified cytokine receptor which are surprisingly suitable for binding studies with ligand candidates and can readily be produced according to conventional crystallization technology. The inventive crystals can be formed at a suitably favorable pH interval and in the presence of a great variety of salts in suitable concentration range. In addition, the crystals have surprisingly favorable characteristics for ligand binding studies. Such an important characteristics are the extension of the crystal packaging surfaces or the contact area between the molecules of the crystal, the solvent uptake capacity, resistance to conventionally employed solvents and their capacity of being frozen with maintained capacity of diffracting during X-ray investigation.

The crystals of the inventive modified cytokine receptors can contain more than 50% (v/v) of a solvent acceptable for binding studies, preferably more than 60% (v/v) of a solvent and even more preferably between 60 to 80% (v/v).

The contact surface between two molecules in the crystal lattice, i.e. the surface buried from solvent, related either by crystallographic or non-crystallographic symmetry, should suitably be in the range 200–1800 Å$^2$. Thus, 100–900 Å$^2$ on each molecule at crystal packing interfaces should be made solvent inaccessible at contacts with other molecules in the crystal lattice. Accordingly, the crystals according to the present invention preferably have a contact surface between two molecules of between 200 to 1800 Å$^2$ (square ångström) and more preferably between 100 to 900 Å$^2$ (square ångström), as determined by surface area calculation performed with the program DSSP (Kabsch & Sander 1983).

The crystals according to the present invention are possible to freeze using nitrogen in liquid or gas form and maintain their capacity of diffracting to at least 3.5 Å and preferably to at least 2.3 Å, or better, when using synchrotron radiation source.

Furthermore, the inventive crystals have an excellent resistance to solvents conventionally used in ligand binding studies. The crystals are resistant to an addition of about 10% (v/v) of dimethylsufoxide (DMSO) or 5% (v/v) of dimethylfluoride (DMF) for at least 24 hours in a crystallization droplet.

A further aspect of the present invention is a method of designing drugs capable of activating cytokine receptor signal transduction activity by employing said inventive crystals in binding studies with selected ligand candidates. In the method, such crystals are preferably soaked with a solution comprising the ligand or co-crystallized with the ligand. The methods may include oligomerization of the receptor induced by specific ligand attraction, such as dimerization of the receptor, when, for example, crystals of a modified growth hormone receptor is investigated with ligands with potential growth hormone activity.

A yet further important aspect of the invention is the provision of a method of obtaining improved cytokine receptor crystals involving the subsequent steps of solving the receptor three-dimensional structure complexed to a ligand by crystallographic methods, identifying regions of the receptor molecule which may contribute to disorder in a crystalline state, producing modified receptor molecules without said regions, and crystallizing the modified receptor without the presence of a ligand. Preferably, in this method, the extracellular part of the receptor has a known primary amino acid sequence and preferably, it is studied when bound to its ligand by conventional crystallographic methods involving such steps as crystallization and X-ray structure determination. Further, such modified proteins can also be used in structural determinations using other techniques such as Nuclear Magnetic Resonance (NMR). From these results it is conceivable to identify domains in the receptor molecule which will contribute to a disordered state in crystalline form and subsequently to produce them deprived of such domains with conventional methods. This method has proved especially successful for human growth hormone receptor initially crystallized with its native ligand human growth hormone.

FIG. 1 schematically illustrates the general features of hGH:hGHR 1:2 complex. A single hormone molecule binds two hGHR molecules at the interface of the two domains. 2700 Å$^2$ becomes solvent inaccessible In hGH site 1-receptor interactions, whereas only 1300 Å$^2$ are covered in site 2 interactions. An additional surface area of 900 Å$^2$ is buried in receptor-receptor interactions of the receptor needed for hormone interactions, 104 and 169, depicted in white. This picture was generated using a 2.5 Å structure of the 1:2 complex, Sundström et al., *J. Biol. Chem.*, 271 (50):32197–203 (1996). All figures were produced using the programs MOLSCRIPT, Collaborative Computations Project Number 4, *Acta Cryst*, D50, 760–63 (1994), RASTER3D, Kraulis, *J. Appl. Cyrst.*, 24, 945–50 (1991), and RENDER, Bacon et al, *J. Molec. Graphics*, 6, 219–20 (1988).

Figure 2A:
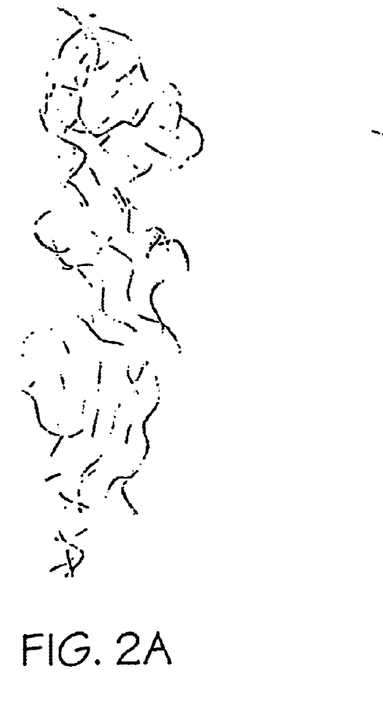
FIGS. 2A and 2B schematically demonstrates side and front views of a comparison of the crystal structures of free hGHR and hGHR interacting with hGH site 1 in the 1:2 complex.
Figure 2B:
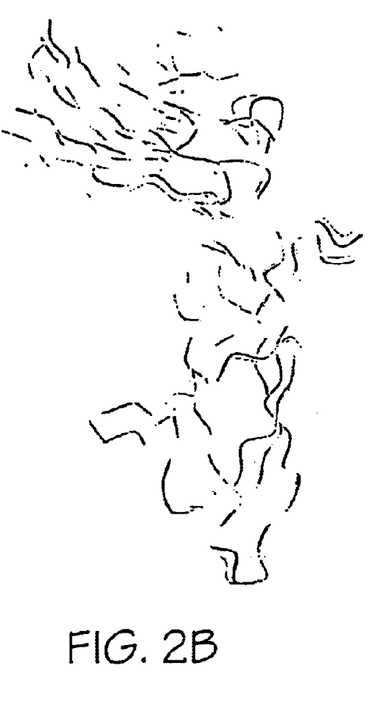

FIGS. 2A and 2B schematically demonstrate a comparison of the crystal structures of free hGHR and hGHR interacting with hGH site 1 in the 1:2 complex. In the structural alignment, only the C-terminal domains were used (residues 128–234) in order to clearly visualize the domain-domain movements upon transitions from free to complexed form, wherein FIG. 2A is a side view and FIG. 2B is a front view. In the free receptor crystal, the two hGHR molecules in the asymmetric unit are very similar with a root mean square deviation of 0.18 Å comparing 184 Ca positions. The corresponding values for the liganded receptors in the 1:2 complex are 1.04 Å (181 Ca positions) and 1.17 Å (172 Ca positions) for the hGH site 1 and site 2 binding receptor respectively.

Figure 3:
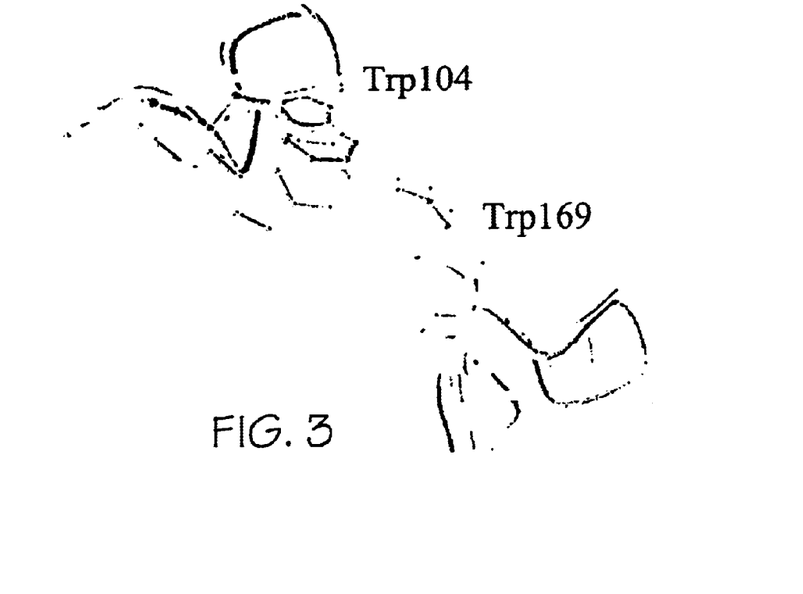
FIG. 3 is a comparison of the conformation of tryptophane residues 104 and 169 as well as adjacent loops.

FIG. 3 is a comparison of the confromation of typtophane residues 104 and 169 as well as adjacent loops. The conformations of TRP169 are virtually identical in both the liganded variants of the receptor. In contrast, Trp104 show distinct conformations and thus is to a greater extent conformationally adapted upon hGH interactions, facilitating high affinity ligand binding. The favorable interdomain hydrogen bond (Glu44–Gln166) only seen in the hGH site 2 binding receptor, is enabled by main and side chain conformational alterations of the loop 163–168. Thus, this loop adaptation may be necessary to allow site 2 interactions to be formed and stabilized.

According to the present invention, new modified hGH binding molecules were engineered to improve crystal forming properties by N- and C-terminal truncations and used to resolve this question at the structural level. The present invention provides the first three dimensional structure of an unliganded hematopoietic receptor determined at 2.3 Å resolution. By putting the present invention into practice, significant structural differences, both in domain orientations and side chain conformations compared to hGH bound receptors are observed, as disclosed below in more detail.

In order to understand the structural requirements for transition of the receptor from an unliganded, monomeric to homodimerized state, investigations were conducted to determine the native free receptor structure. However, despite strenuous efforts all attempts failed to crystallize the native molecule, hGHR$_{1-237}$ (consisting of residues 1–237 of the hGHR extracellular domain). In order to provide modified receptor molecules more suitable for structural studies, the 2.5 Å resolution structure of the hGH:hGHR 1:2 complex described in Sundström et al, (1996) was initially studied. It was found that the first 31 residues at the N-terminus of hGHR could be disordered in the crystal structure of both receptor molecules in the 1:2 complex. In addition, this region is susceptible to proteolytic degradation. Therefore, the N-terminal of the domain region was truncated, and the modified molecules were subjected to crystallization preformance test. In surprising contrast, the truncated hGHR$_{32-237}$ crystalliezed readily, although not of diffraction quality. Additional residues found at the C-terminal and disordered in the 1:2 complex, thereby potially contributing to the disorder of the free receptor molecule, were removed to create a second generation of molecules truncated at the C-terminus. One such receptor variant, hGHR$_{32-234}$ not only yielded crystals of surprisingly good diffraction quality (Table 1) but also displayed surprisingly improved properties with regard to expression levels, solubility and stability during the purification process. Moreover, the N-terminal truncation yields a molecule similar in sequence to the naturally occurring hGHR exon-3 splice variant discussed in both *Mol. Endocrinol.*, 1992, Vol. 6, p. 279–87, and *J. Biol Chem.*, 1993, Vol. 268, p. 19025–32, by M. Urbankek et al. It was also confirmed that the truncated hGHR variants bind hGH with the same stoichiometry and very similar affinity as the native molecule.

The crystals obtained contain more than 60% (v/v) solvent and have only minor interactions with neighboring molecules in the crystal lattice. Thus, the unliganded receptor structure is highly suitable for structural comparisons. In addition, crystal soaking experiments are highly feasible, since spacious solvent channels within the crystals will allow diffusion of small hGH mimicking ligand molecules to the receptor.

The modified receptors according to the present invention have enabled, for the first time, detailed comparisons of inactive or unliganded receptors in comparison with the active or liganded form. By means of the present invention, several new findings therefore are presented below which clearly demonstrate its considerable importance for understanding the molecular mechanisms of receptor activation. In particular, it is crucial to be provided with a structural basis for receptor activation.

As revealed by de Vos et al., (1992), the two extracellular domains of the receptor have topologies similar to the fibronectin type III fold. In the 1:2 complex of hGH with hGHR, the two receptor molecules are very similar to each other. In the crystal structure of the 1:1 complex of an hGH antagonist mutant (where Gly 120 has been substituted with an arginine-hGH-G120R), with hGHR, the structure of the receptor is remarkably similar to the corresponding molecule in the 1:2 complex, Sundström et al.,(1996) These structural studies suggest that no significant conformational changes of the hGH site 1 binding receptor occurs upon binding of the second receptor. Although the 1:2 complex structure revealed that it is possible that binding of hGH could influence the domain orientation of the receptor, de Vos et al., (1992), it has been suggested that no large conformational adaptations of either hGH or hGHR would occur when the ternary complex is formed, Wells, J. A., *Curr. Opin. Cell Biol.*, Vol. 6, p. 163–173 (1994).

It was also observed that the domain orientation differed significantly, when comparing the structures of liganded and unliganded hGHR. When a structural alignment of the C-terminal domains (residues 128–234) is made, a large shift in the N-terminal domain (residues 32–123) between ligand bound and free receptor form is observed. The angle between the two domains is considerably higher (7°) in the free receptor form than for the receptor molecules in the 1:2 and 1:1 complexes. Thus, the corresponding atom positions are translated 4 Å vertically and 2.5 Å horizontally, comparing residues furthest away from the interdomain connecting loop (FIG. 2).

T. Clackson and J. A. Wells, in *Science*, Vol. 267, p. 383–386(1995), identified Trp104 and Trp169 in the receptor as the key residues in hormone binding. Since hGH can interact with the receptor using two distinct binding sites, the loop containing Trp104 occupies two different conformations to enable receptor homodimerisation. In the unliganded receptor, the conformations of main and side chains in the loop containing Trp104 are similar to the conformation observed in the receptor binding to hGH site 2 (FIG. 3). Therefore, the hGH site 1 interactions induced a conformational adaptation of the Trp104 side chain and its loop region to a greater extent than the hGH site interactions. In contrast, the conformation of Trp169 is very similar in the free and the liganded receptor molecules (FIG. 3). The structural rigidity of Trp169 could suggest a role for this residue in the initial hormone-receptor recognition event. However, compared to its conformation in the unliganded receptor, the loop preceding Trp169 (residues 163–168) conformationally adapts only upon hGH site 2 interactions, remaining essentially unchanged at hGH site 1. The structural adaptations of the two loop regions (102–106 and 163–168) in the receptor seem to enable binding to hGH binding site 1 and 2, respectively.

In the unliganded receptor, favorable interdomain interactions can be observed between Arg39 NH1-Gln130 O (2.4 Å), Arg39 NH2-Asp132 Od1 (3.2 Å), Ser40 N-Ile128 O (2.8 Å), Arg43 NH1-Trp169 O (2.7 Å) and Arg43 NH2-Trp169 Ne1 (3.2 Å). Another key residue, Asp126, contributes indirectly by stabilizing the conformation of Arg43. Essentially the same interactions are observed in both liganded receptors in the 1:2 complex, but with some differences in apparent bond lengths. An additional interdomain interaction, Glu44 Oe1-Gln166 Ne2 (2.8 Å), is observed only in the hGH site 2 binding receptor and is most likely facilitated by structural adaptation of the loop 163–168. Hence, the observed differences in domain orientations between liganded and unliganded receptors seem to be only to a minor extent caused by forming and breaking of interdomain hydrogen bond interactions. Since a certain degree of domain flexibility appears to be an inherent property of the extracellular part of hGHR, fine tuned adjustments in interdomain interactions could contribute significantly to the domain rearrangement upon ligand binding. In this context, it is important to stress the fact that virtually no crystal packing interactions from adjacent molecules in the crystal lattice can be observed in regions predicted to be essential for domain-domain interactions or hGH binding in the present study.

Through the percise structure of native hGH in its unliganded form is unknown, the crystal structure of a hGH site 1 high affinity mutant, developed by M. H. Ultsch et al., in *J. Mol. Biol.*, Vol 236, p. 286–99 (1944), revealed that the structure hormone in the absence of receptor interactions was similar to the receptor bound native molecule. Additionally, in the 1:1 complex, the N-terminus (residues 1–6) of hGH-G120R was observed to occupy a significantly different conformation in the absence of the receptor interactions and thus is conformationally adapted upon formation of the ternary complex. Other differences between the hormone molecules in the 1:1 and the 1:2 complex are minor.

Another cytokine receptor, the erythropoietin receptor (EPOR) was found by S. S. Watowich et al., in *Mol. Cell Biol.*, Vol. 14, p. 3535–49 (1994) to be constitutively active when disulfide-linked homodimers are formed in the extracellular domain. O. Livnah et al., in *Science*, Vol. 273p.

464–71 (1996) and N. C. Wrighton et al., in *Science* Vol. 273, p. 458–63 (1996), demonstrated that cyclic peptides derived from phage display screening could dimerize and activate the EPOR[13,14] as well as can association of the EPOR with a virus glycoprotein[15]]EROP. A. D. D'Andrea, in *Cancer Surv.*, Vol 15, p. 19–36 (1992), demonstrated this effect using a virus glycoprotein, as well. Since no similar mechanisms have been reported for hGHR, the mode of EPOR activation appears promiscuous compared to growth hormone receptors. The PRLR and EPOR structures revealed by W. Somers in *Nature*, Vol. 372, p. 478–81 (1994), A. A. Kossiakoff et al. in *Protein Science*, Vol. 3, p. 1697–1705, (1994), and O. Livnah in *Science* (1996) to have significantly different domain orientations of the receptors compared to the hGHR. Since the PRLR interact with both prolactin and hGH, structural adaptations of the receptor molecule could facilitate binding of these two related but distinct hormone ligands.

Structural adaptations of hGHR upon ligand binding could serve several functions. Obviously one is to provide the specificity and affinity needed for the interaction Another possibility suggested by S. J. Frank et al. in *Endocrinology*, Vol. 135, p. 148–156 (1994), is that the interdomain rearrangement enables the formation of disulfide linked receptor dimers upon hGH exposure. Ligand induced hGHR conformational adaptation could thus facilitate receptor dimerization and be an important mechanism to keep unliganded receptors inactive. Since, according to C. H. Heldin in *Cell*, Vol. 80, p. 213–223 (1995), dimerization of cell surface receptors most likely is a general mechanism to initiate intracellular signal transduction, conformational adaptation of receptor molecules upon ligand binding, as observed in this study, may be applicable to other systems as well. The invention as described in the appended claims, therefore should be regarded as generalizible beyond the claim scope.

EXAMPLE 1 hGH and hGHR used in the protein crystallographic work were expressed and purified as previously described in Sundström et al, (1996). Truncation mutants of hGHR were created using standard sub-cloning techniques and the expressed protein was assayed for hGH binding using affinity and size exclusion gel filtration chromatography as well as BIAcore (Pharmacia Biosensor, Sweden) measurements. The hGHR$_{32-234}$ (SEQ ID NO: 3) protein was crystallized by vapor diffusion, using 3 ml protein solution (7 mg/ml in 10 mM ammonium acetate) mixed with 3 ml of 0.33 M NH$_4$SO$_4$, 30% (w/v) PEG-2000-dimethyl ether, 1% (v/v) DMSO and 100 mM MES buffer at pH 6.4 in a sealed tissue culture 24-well plate (Falcon, USA). The crystallization droplets were equilibrated at +18° C. with 1 ml of the mother liquor for 2–4 weeks to obtain optimal quality crystals that diffracted to at least 2.9 Å with a conventional X-ray source. The crystals could be frozen directly in the N$_2$ beam by adding a 1:1 mixture of 25% (v/v) ethylene glycol and 25% glycerol (v/v) to the crystallization droplet. Data was collected at station A1 at Cornell High Energy Synchrotron Source using a CCD detector (Area Detector Systems Corp., USA). The data was indexed, processed and scaled in the tetragonal spacegroup 14 using the programs DENZO and SCALEPACK, developed by S. Bailey in the SECR Daresbury Laboratory, Warrington, 1993. A molecular replacement search procedure was performed using the program AMORE, also developed by Bailey, 1993. The co-ordinates of the site 1 binding hGHbp molecule in our 2.5 Å hGH:hGHR 1:2 complex was used. The highest scoring solution in the resolution interval 8–4 Å was found in space group 14 with two hGHbp molecules in the asymmetric unit. A rigid-body refinement in X-plor, described by J. Navaza in *Acta Cryst.*, 1994, Vol. A (50), pp. 157–163, with individual hGHbp domains including data between 10–6, 10–5 and 10–3.5 Å in each respective cycle, decreased both the R- and Free-R values (described by A. T. Brünger in *Nature*, 1992, Vol. 335, pp. 472–475) dramatically when compared to previous runs where the native hGHbp domain arrangement had been used. A cyclic process of model building in O, described by Brünger, 1992, followed by NCS restrained POWELL minimization in X-plor using data between 15–2.3 Å, corrected for most main and side chain changes to the search molecule. At this stage, the first simulated annealing run, as described by T. A. Jones et al. in *Acta Cryst*, 1991, Vol. A(47), pp. 110–119, was performed using a slow-cooling protocol from 3000 K to 300K in 50 Ps steps. Solvent molecules were introduced into FoFc densities above 3.0 s. After 3 cycles, a total of 327 solvent molecules had been introduced and assigned to the protein chain using the programs DISTANG and WATERTIDY developed by A. T. Brünger et al., 1989, in the CCP4 program package. A final POWELL minimization was preformed, followed by a simulated annealing run from 2500 K to 300 K in 50 Ps steps including data between 15 to 2.3 Å. Individual B-value refinement was added as the final step, and solvent molecules with high temperature factors, greater than 50 Å$^2$, or absent 2FoFc electron densities at 1.0 s, were removed. The Free-R value was used to validate the progress of the entire refinement. The final model consists of residues 32–52, 63–70 and 80–234 of both molecules in the asymmetric unit as well as 261 solvent molecules and two sulphate ions. At the present stage of refinement the R-factor of the model is 21.7% (R-free 29.3%) using data between 10–2.3 Å. As a control, a dataset to 3.2 Å at room temperature was collected. No significant differences to the 2.3 Å structure were observed showing that the transfer to cryogenic conditions did not induce conformational adaptation. See also, Merritt et al, *Acta. Cryst.*, D50, 869–73 (1994).

TABLE 1

| Crystallographic data for hGHR$_{32-234}$ (SEQ ID NO: 3) | |
|---|---|
| No of crystals: | 1 |
| Resolution: | 2.3 Å |
| Completeness | 89.7% (18–2.3 Å) |
| | 87.1% (2.4–2.3 Å) |
| Multiplicity: | 4.8 |
| Rmerge | 6.7% (18–2.3 Å) |
| | 24.6% (2.4–2.3 Å) |
| Cell | 104.8 104.8 115.7 Å |
| | 90° 90° 90° |
| Space group | I4 |
| No of solvent molecules | 261 |
| Unique reflections | 24987 |
| r.m.s bond deviations (Å) | 0.011 |
| r.m.s angle deviations (°) | 1.76 |
| model R-factor/R-free | 21.7/29.3% |

What is claimed is:

1. A human growth hormone receptor (hGHR) consisting of residues 32–237 (SEQ ID NO: 2), 32–234 (SEQ ID NO: 3), or 34–233 (SEQ ID NO: 4), of the native hGHR molecule.

2. A human growth hormone receptor (hGHR) according to claim 1 consisting of residues 32–237 (SEQ ID NO: 2), of the native hGHR molecule.

* * * * *

UNITED STATES PATENT AND TRADEMARK OFFICE
CERTIFICATE OF CORRECTION

PATENT NO. : 6,891,025 B2
DATED : May 10, 2005
INVENTOR(S) : Sundström et al.

It is certified that error appears in the above-identified patent and that said Letters Patent is hereby corrected as shown below:

Column 13,
Line 40, change "or 34-23 3 (SEQ ID NO: 4)" to -- or 34-233 (SEQ ID NO: 4) --.

Signed and Sealed this

Twenty-sixth Day of July, 2005

JON W. DUDAS
*Director of the United States Patent and Trademark Office*

SEQUENCE LISTING

<160> NUMBER OF SEQ ID NOS: 4

<210> SEQ ID NO 1
<211> LENGTH: 237
<212> TYPE: PRT
<213> ORGANISM: Homo sapiens

<400> SEQUENCE: 1

```
Met Asp Leu Trp Gln Leu Leu Thr Leu Ala Leu Ala Gly Ser Ser
1               5                   10                  15

Asp Ala Phe Ser Gly Ser Glu Ala Thr Ala Ala Ile Leu Ser Arg Ala
                20                  25                  30

Pro Trp Ser Leu Gln Ser Val Asn Pro Gly Leu Lys Thr Asn Ser Ser
                35                  40                  45

Lys Glu Pro Lys Phe Thr Lys Cys Arg Ser Pro Glu Arg Glu Thr Phe
            50                  55                  60

Ser Cys His Trp Thr Asp Glu Val His His Gly Thr Lys Asn Leu Gly
65                  70                  75                  80

Pro Ile Gln Leu Phe Tyr Thr Arg Arg Asn Thr Gln Glu Trp Thr Gln
                85                  90                  95

Glu Trp Lys Glu Cys Pro Asp Tyr Val Ser Ala Gly Glu Asn Ser Cys
            100                 105                 110

Tyr Phe Asn Ser Ser Phe Thr Ser Ile Trp Ile Pro Tyr Cys Ile Lys
            115                 120                 125

Leu Thr Ser Asn Gly Gly Thr Val Asp Glu Lys Cys Phe Ser Val Asp
        130                 135                 140

Glu Ile Val Gln Pro Asp Pro Pro Ile Ala Leu Asn Trp Thr Leu Leu
145                 150                 155                 160

Asn Val Ser Leu Thr Gly Ile His Ala Asp Ile Gln Val Arg Trp Glu
                165                 170                 175

Ala Pro Arg Asn Ala Asp Ile Gln Lys Gly Trp Met Val Leu Glu Tyr
            180                 185                 190

Glu Leu Gln Tyr Lys Glu Val Asn Glu Thr Lys Trp Lys Met Met Asp
        195                 200                 205

Pro Ile Leu Thr Thr Ser Val Pro Val Tyr Ser Leu Lys Val Asp Lys
    210                 215                 220

Glu Tyr Glu Val Arg Val Arg Ser Lys Gln Arg Asn Ser
225                 230                 235
```

<210> SEQ ID NO 2
<211> LENGTH: 206
<212> TYPE: PRT
<213> ORGANISM: Homo sapiens

<400> SEQUENCE: 2

```
Ala Pro Trp Ser Leu Gln Ser Val Asn Pro Gly Leu Lys Thr Asn Ser
1               5                   10                  15

Ser Lys Glu Pro Lys Phe Thr Lys Cys Arg Ser Pro Glu Arg Glu Thr
                20                  25                  30

Phe Ser Cys His Trp Thr Asp Glu Val His His Gly Thr Lys Asn Leu
            35                  40                  45

Gly Pro Ile Gln Leu Phe Tyr Thr Arg Arg Asn Thr Gln Glu Trp Thr
        50                  55                  60

Gln Glu Trp Lys Glu Cys Pro Asp Tyr Val Ser Ala Gly Glu Asn Ser
65                  70                  75                  80
```

```
Cys Tyr Phe Asn Ser Ser Phe Thr Ser Ile Trp Ile Pro Tyr Cys Ile
                 85                  90                  95

Lys Leu Thr Ser Asn Gly Gly Thr Val Asp Glu Lys Cys Phe Ser Val
            100                 105                 110

Asp Glu Ile Val Gln Pro Asp Pro Ile Ala Leu Asn Trp Thr Leu
            115                 120                 125

Leu Asn Val Ser Leu Thr Gly Ile His Ala Asp Ile Gln Val Arg Trp
130                 135                 140

Glu Ala Pro Arg Asn Ala Asp Ile Gln Lys Gly Trp Met Val Leu Glu
145                 150                 155                 160

Tyr Glu Leu Gln Tyr Lys Glu Val Asn Glu Thr Lys Trp Lys Met Met
                165                 170                 175

Asp Pro Ile Leu Thr Thr Ser Val Pro Val Tyr Ser Leu Lys Val Asp
                180                 185                 190

Lys Glu Tyr Glu Val Arg Val Arg Ser Lys Gln Arg Asn Ser
                195                 200                 205

<210> SEQ ID NO 3
<211> LENGTH: 203
<212> TYPE: PRT
<213> ORGANISM: Homo sapiens

<400> SEQUENCE: 3

Ala Pro Trp Ser Leu Gln Ser Val Asn Pro Gly Leu Lys Thr Asn Ser
1               5                   10                  15

Ser Lys Glu Pro Lys Phe Thr Lys Cys Arg Ser Pro Glu Arg Glu Thr
                20                  25                  30

Phe Ser Cys His Trp Thr Asp Glu Val His His Gly Thr Lys Asn Leu
            35                  40                  45

Gly Pro Ile Gln Leu Phe Tyr Thr Arg Arg Asn Thr Gln Glu Trp Thr
        50                  55                  60

Gln Glu Trp Lys Glu Cys Pro Asp Tyr Val Ser Ala Gly Glu Asn Ser
65                  70                  75                  80

Cys Tyr Phe Asn Ser Ser Phe Thr Ser Ile Trp Ile Pro Tyr Cys Ile
                85                  90                  95

Lys Leu Thr Ser Asn Gly Gly Thr Val Asp Glu Lys Cys Phe Ser Val
            100                 105                 110

Asp Glu Ile Val Gln Pro Asp Pro Ile Ala Leu Asn Trp Thr Leu
            115                 120                 125

Leu Asn Val Ser Leu Thr Gly Ile His Ala Asp Ile Gln Val Arg Trp
130                 135                 140

Glu Ala Pro Arg Asn Ala Asp Ile Gln Lys Gly Trp Met Val Leu Glu
145                 150                 155                 160

Tyr Glu Leu Gln Tyr Lys Glu Val Asn Glu Thr Lys Trp Lys Met Met
                165                 170                 175

Asp Pro Ile Leu Thr Thr Ser Val Pro Val Tyr Ser Leu Lys Val Asp
                180                 185                 190

Lys Glu Tyr Glu Val Arg Val Arg Ser Lys Gln
                195                 200

<210> SEQ ID NO 4
<211> LENGTH: 202
<212> TYPE: PRT
<213> ORGANISM: Homo sapiens

<400> SEQUENCE: 4
```

-continued

```
Ala Pro Trp Ser Leu Gln Ser Val Asn Pro Gly Leu Lys Thr Asn Ser
1               5                   10                  15

Ser Lys Glu Pro Lys Phe Thr Lys Cys Arg Ser Pro Glu Arg Glu Thr
            20                  25                  30

Phe Ser Cys His Trp Thr Asp Glu Val His His Gly Thr Lys Asn Leu
        35                  40                  45

Gly Pro Ile Gln Leu Phe Tyr Thr Arg Arg Asn Thr Gln Glu Trp Thr
    50                  55                  60

Gln Glu Trp Lys Glu Cys Pro Asp Tyr Val Ser Ala Gly Glu Asn Ser
65                  70                  75                  80

Cys Tyr Phe Asn Ser Ser Phe Thr Ser Ile Trp Ile Pro Tyr Cys Ile
            85                  90                  95

Lys Leu Thr Ser Asn Gly Gly Thr Val Asp Glu Lys Cys Phe Ser Val
            100                 105                 110

Asp Glu Ile Val Gln Pro Asp Pro Pro Ile Ala Leu Asn Trp Thr Leu
            115                 120                 125

Leu Asn Val Ser Leu Thr Gly Ile His Ala Asp Ile Gln Val Arg Trp
    130                 135                 140

Glu Ala Pro Arg Asn Ala Asp Ile Gln Lys Gly Trp Met Val Leu Glu
145                 150                 155                 160

Tyr Glu Leu Gln Tyr Lys Glu Val Asn Glu Thr Lys Trp Lys Met Met
            165                 170                 175

Asp Pro Ile Leu Thr Thr Ser Val Pro Val Tyr Ser Leu Lys Val Asp
            180                 185                 190

Lys Glu Tyr Glu Val Arg Val Arg Ser Lys
            195                 200
```